United States Patent [19]
Yokoi

[11] Patent Number: 5,833,636
[45] Date of Patent: Nov. 10, 1998

[54] SPLINT

[75] Inventor: Isao Yokoi, Aichi-ken, Japan

[73] Assignee: Softwave, Inc., Gifu-ken, Japan

[21] Appl. No.: 672,547

[22] Filed: Jun. 28, 1996

[30] Foreign Application Priority Data

Apr. 3, 1996 [JP] Japan .................................. 8-108387

[51] Int. Cl.⁶ .................................................. A61F 5/04
[52] U.S. Cl. ................................................................ 602/5
[58] Field of Search ................................ 602/5, 6, 7, 8

[56] References Cited

U.S. PATENT DOCUMENTS 4,628,917  12/1986  Campagna, Jr. et al. ................... 602/8
4,977,816  12/1990  Murabayashi et al. ...................  521/92

FOREIGN PATENT DOCUMENTS 58-4485   1/1983   Japan .

*Primary Examiner*—Richard J. Apley
*Assistant Examiner*—Kim Lee
*Attorney, Agent, or Firm*—Cushman Darby & Cushman Intellectual Property Group of Pillsbury Madison & Sutro LLP

[57] ABSTRACT

A splint comprises a core made of a thin metallic rod and a cushion made of resinous foam for covering upper and lower sides of the core. The cushion has an injury-facing side which forms a gutter-shaped concave.

8 Claims, 4 Drawing Sheets

SPLINT

BACKGROUND OF THE INVENTION

The priority document, Japanese Patent Application No. 8-108387, filed in Japan on Apr. 3, 1996, is hereby incorporated by reference into the present specification.

1. Field of the Invention

This invention relates to a splint to be used for setting injuries of the arms or legs and to immobilize healing appendages.

2. Description of Related Art

A conventional splint comprising a ladder-shaped wire core encased in a resinous foam cushion is generally known. As shown in FIGS. 4 and 5, a splint 51 comprising a ladder-shaped core 52, a cushion 53 which covers the core 52, and a piled fabric 54 (for instance toweling) adhered to the injury-facing side of the cushion 53 is also known (Japanese Utility Model Publication No. 58-4485).

Conventional splints have, however, the following problems.

(1) Lack of Ergonomic Consideration. As shown in FIG. 6, despite the rounded, convex shape of a leg (or a arm) 55, the splint 51 is level. The level shape of the splint 51 is not conducive to close, comfortable fittings when it is applied to the leg 55. Furthermore, the level shape of the splint 51 makes it difficult to be wound and fixed with a bandage 56 to the leg 55, or it requires an inordinate length of bandaging.

(2) Necessity of Extra Bandage on the Splint Before Application to Injury. Since a cushion made of resinous foam has low absorbency for perspiration from the injury site, it is commonly wound in a bandage having high absorbency before its application to the injury and subsequently winding it with another bandage, which requires extra time and labor. According to the splint 51 of the above-mentioned Japanese Utility Model Publication No. 58-4485, the piled fabric 54 that is adhered to the injury-facing side of the cushion 53 adequately absorbs perspiration. However, an extra bandage 57 for winding the splint 51 before its application to the injury is still required because of the fear that the cushion 53 might be exposed by the injury-facing side when the piled fabric 54 sloughs off; or that the ladder-shaped core 52 might be exposed when the cushion 53 is torn as might occur if the piled fabric 54 sloughs off. Or, the cushion 53 might be torn by the side opposite to the injury-facing side.

(3) Lack of Deodorant. Conventional technology lacks deodorant protection. Consequently, upon absorbing perspiration and the resulting bacteria, an offensive odor results in a conventional splint, which can give an unpleasant feeling to a patient using the splint and his nursing people.

SUMMARY OF THE INVENTION

It is, therefore, an object of this invention to provide a splint which is conducive to close, comfortable fittings when it is applied to the arms or legs, and which can be easily wound and fixed with a bandage to the arms or legs.

Another object of this invention is to provide a splint which is superior in absorbing perspiration without an extra bandage for winding the splint before its application to injuries, thereby enabling its direct application to injury, and which brings no fear that the cushion or the ladder-shaped core might be exposed after being applied to the arms or legs.

Still another object of this invention is to provide a splint which can diminish the occurrence of perspiration-induced bacterial odors.

In order to attain these objects, this invention provides a splint comprising a core made of a thin metallic rod and a cushion made of resinous foam for covering upper and lower sides of the core, wherein the cushion has an injury-facing side which forms a gutter-shaped concave. The gutter-shaped concave is not limited to an exact cylindrical shape, but it may, for example, be v-shaped.

The following are examples of the method for shaping the injury-facing side of the cushion into the gutter-shaped concave.

(1) Forming a core level, and covering the upper side of the core with a cushion whose injury-facing side forms a gutter-shaped concave.

(2) Forming both a core and a cushion level, and bending the core plastically, thereby shaping the injury-facing side of the cushion into a gutter-shaped concave.

Another preferred embodiment of the invention provides a splint comprising a core made of a thin metallic rod and a cushion made of resinous foam for covering upper and lower sides of the core, wherein the cushion is wholly covered in a sack-shaped fabric. The cushion and the sack-shaped fabric may or may not be adhered together.

As long as the sack-shaped fabric is highly absorbent of perspiration, its material is not limited to a particular type. However, cotton is preferable. A weave style of the sack-shaped fabric is also not limited to a particular type. However, a stretchable one, for example, knitted type is preferable.

The above mentioned preferred embodiments of the invention can be combined together to provide a splint wherein the cushion has an injury-facing side which forms a gutter-shaped concave and the cushion is wholly covered in a sack-shaped fabric.

When the cushion is wholly covered in the sack-shaped fabric, it is preferable to sandwich a deodorant sheet, an antibacterial sheet or a deodorant antibacterial sheet between the injury-facing side of the cushion and the sack-shaped fabric.

Examples of the deodorant sheet include a sheet containing deodorant matter which physically adsorbs or chemically removes odorous materials. The antibacterial sheet is a sheet containing antibacterial matter which restricts bacterial breeding, thereby diminishing the occurrence of offensive odors. The deodorant antibacterial sheet contains both deodorant and antibacterial matter. Examples of the materials from which these sheets may be made include non-woven fabric, woven fabric, or waterproof paper.

Further objects of this invention will become evident upon an understanding of the illustrative embodiment described below. Various advantages not specifically referred to herein but within the scope of the instant invention will occur to one skilled in the art upon practice of the presently disclosed invention. The following example and embodiment are illustrative and not seen to limit the scope of the invention.

DETAILED DESCRIPTION OF THE PREFERRED EMBODIMENTS

Figure 1:
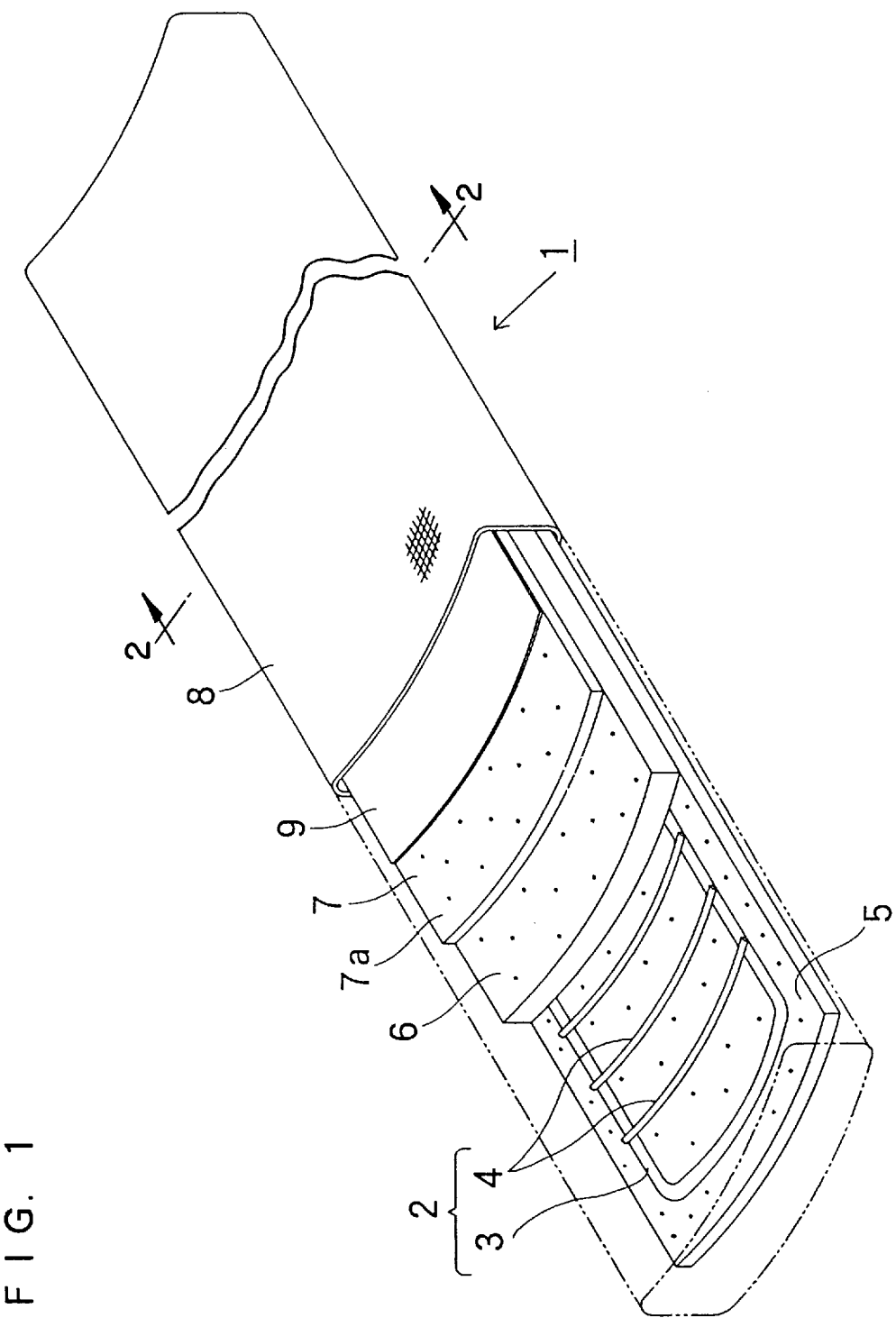
FIG. 1 is a perspective view of a splint embodying the invention.
Figure 2:
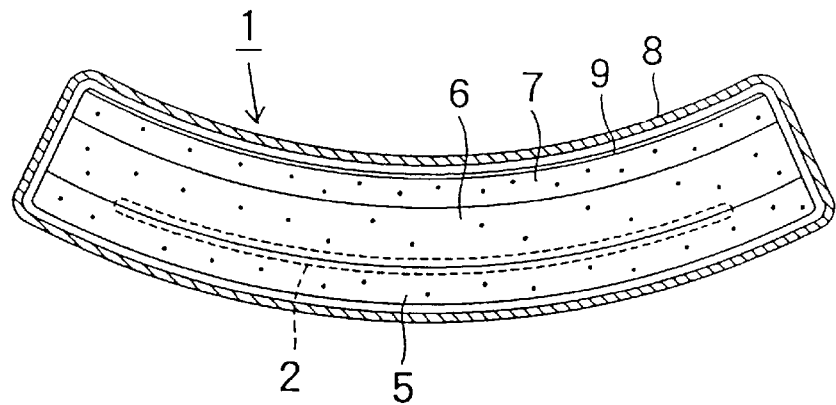
FIG. 2 is a sectional view of the splint of FIG. 1.

Description will now be made of a splint embodying the invention with reference to FIGS. 1 to 3. A splint 1 comprises a ladder-shaped core 2. The core 2 comprises a frame 3, which is obtained by bending and welding a thin metallic rod to form a long and narrow rectangle, and a number of steps 4, 4 . . . , both ends of which are welded onto the longer, parallel sides of the frame 3 with a clearance of 2 to 4 cm therebetween.

A belt-shaped lower cushion 5 made of soft polyurethane foam is affixed to the lower side of the core 2. A belt-shaped upper first cushion 6 made of rubberthane foam (rubberthane foam is a hybrid material mode of polyurethane foam and ethereal synthetic rubber or natural rubber), which is harder than the lower cushion 5, is affixed to the upper side of the core 2. Affixed to the upper side of the upper first cushion 6 is a belt-shaped upper second cushion 7 made of soft polyurethane foam, which is as soft as the lower cushion 5. Thus, the core 2 is completely covered with these cushions 5, 6 and 7. It should be noted that cushions for covering the core 2 are not limited to the above mentioned materials and structure sequence. For example, variations in the number of layers of cushions on the upper side of the core 2 (such as, one or three layers) may be appropriate.

The core 2 and cushions 5, 6 and 7 are formed level at first. The cushions 5, 6, and 7 are affixed to the core 2 to cover upper and lower sides thereof, thus resulting in an initially horizontally level unit. The steps 4, 4 . . . and both ends of the frame 3 of the core 2 are then plastically bent by a processing apparatus (not shown), which is accompanied by the bend of the cushions 5, 6 and 7, thereby resulting in a gutter-shaped concave of the injury-facing side 7a of the upper second cushion 7.

The cushions 5, 6 and 7 are wholly covered in a sack-shaped fabric 8; however, the sack-shaped fabric 8 is not adhered to the cushions 5, 6, and 7. The sack-shaped fabric 8 is obtained by sewing a knitted, cotton material with cotton thread to give a sack having an opening, which fits snugly around the cushions 5, 6, and 7 in the shape of an unit as a whole, inserting the cushions 5, 6 and 7 into the sack from the opening, and then sewing the opening. Thus obtained sack-shaped fabric 8 is very stretchable and highly absorbent of perspiration.

As a belt-shaped deodorant antibacterial sheet 9, "SEMIA", which is a trade name of a product manufactured by ASAHI CHEMICAL INDUSTRY CO., LTD., is sandwiched between the injury-facing side 7a of the upper second cushion 7 and the sack-shaped fabric 8. "SEMIA" is a sheet of non-woven fabric having high durability embedded with both deodorant and antibacterial matter. "SEMIA" 's deodorant effect for various odorous materials such as ammonia, hydrogen sulfide, methyl mercaptan and trimethylamine has been confirmed. "SEMIA" 's antibacterial effect for miscellaneous bacteria such as yellow staphylococcus has also been confirmed.

The splint 1 of the present invention as described above has the following advantages.

Figure 3:
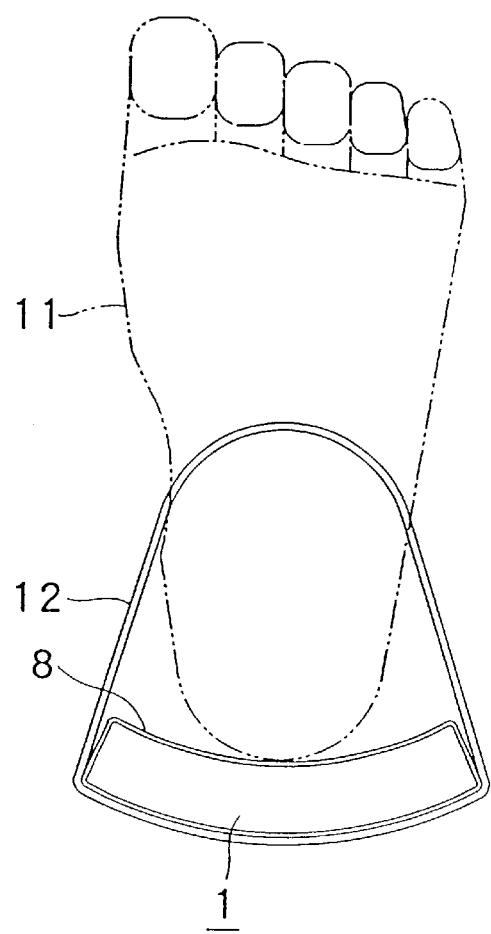
FIG. 3 is a schematic view of the splint of FIG. 1, in use.
Figure 4:
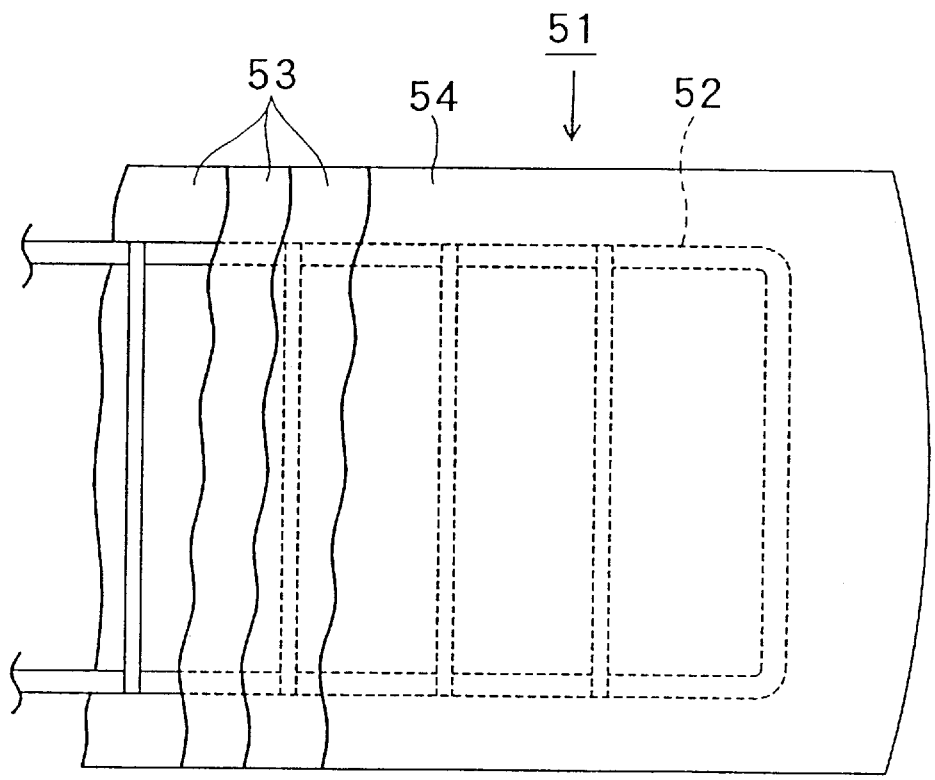
FIG. 4 is a plan view of a conventional splint.
Figure 5:
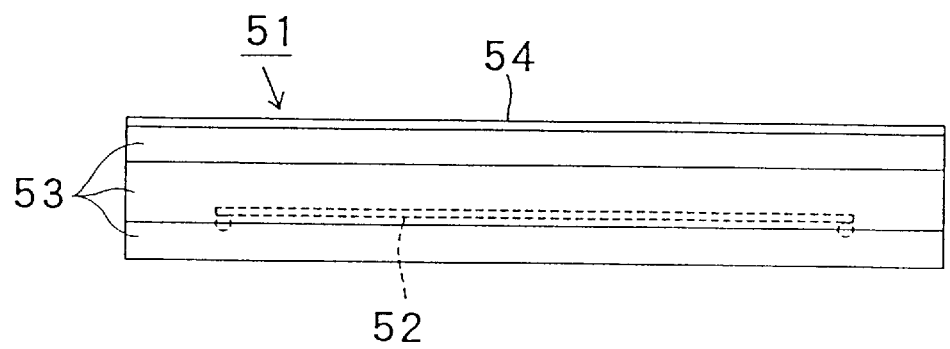
FIG. 5 is a end view of the splint of FIG. 4.
Figure 6:
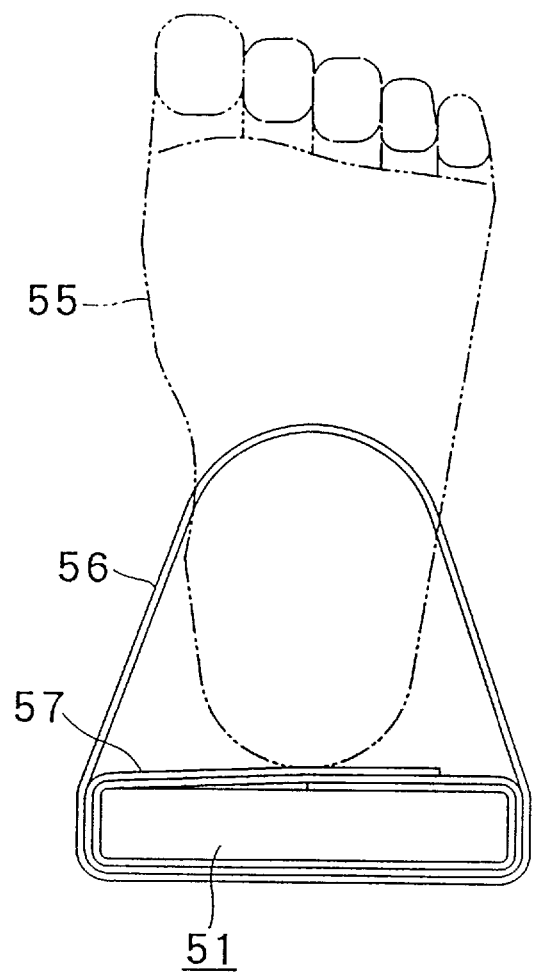
FIG. 6 is a schematic view of the splint of FIG. 4, in use.

(1) Because of the gutter-shaped concave of the injury-facing side 7a of the upper second cushion 7, as is shown in FIG. 3, the splint 1 is conducive to close, comfortable fittings when it is applied to a leg (or an arm) 11 along its periphery, and it can be easily wound and fixed with a bandage 12 to the leg 11. Moreover, since the lower side (opposite to the injury-facing side) of the lower cushion 5 is also bent, the length of the bandage 12 can be shorter than that required for conventional splints having level shape.

(2) All of cushions 5, 6, and 7 are wholly covered with the sack-shaped fabric 8. Thus there is no fear that the sack-shaped fabric 8 may slough off and that the upper second cushion 7 may be exposed. Even if the cushion 5 is torn, the core 2 is not exposed, because of the sack-shaped fabric 8. Therefore, the splint 1 can be safely and directly applied to an injury without being wound in an extra bandage that is required for conventional splints. The sack-shaped fabric 8 stretches according to the splint 1 that is transformed to the fit to injury, and absorbs perspiration well.

(3) The deodorant antibacterial sheet 9 restricts bacterial breeding and adsorbs odorous materials, thereby diminishing the occurrence of offensive odors. Thus, patients using the splint 1 and their nursing people are not annoyed with offensive odors.

As many apparently widely different embodiments of this invention may be made without departing from the spirit and scope thereof, it is to be understood that the invention is not limited to the specific embodiments thereof except as defined in the appended claims.

What is claimed is:

1. A splint comprising:

a core made of a thin metallic rod;

a cushion made of resinous foam that covers an upper and a lower side of said core; and a sack-shaped fabric, wherein said cushion has an injury-facing side which is formed with a concavity and said cushion is wholly covered in said sack-shaped fabric, wherein said cushion and said sack-shaped fabric are adhered together.

2. A splint as set forth in claim 1, wherein said gutter-shaped concave of said injury-facing side of said cushion is formed by forming both said core and said cushion to be level and bending said core plastically.

3. A splint comprising:

a core made of a thin metallic rod;

a cushion made of resinous foam that covers an upper and a lower side of said core; and a sack-shaped fabric, wherein said cushion has an injury-facing side which is formed with a concavity and said cushion is wholly covered in said sack-shaped fabric, wherein said sack-shaped fabric is made of a material which is highly absorbent of perspiration.

4. A splint as set forth in claim 3, wherein said core is formed to be level and the upper side of said core is covered with said cushion whose injury-facing side forms a gutter-shaped concave.

5. A splint as set forth in claim 3, wherein said cushion and said sack-shaped fabric are not adhered together.

6. A splint as set forth in claim 3, wherein a deodorant sheet is sandwiched between said injury-facing side of said cushion and said sack-shaped fabric.

7. A splint as set forth in claim 3, wherein an antibacterial sheet is sandwiched between said injury-facing side of said cushion and said sack-shaped fabric.

8. A splint comprising:

a core made of a thin metallic rod;

a cushion made of resinous foam that covers an upper and a lower side of said core; and a sack-shaped fabric, wherein said cushion has an injury-facing side which is formed with a concavity and said cushion is wholly covered in said sack-shaped fabric, wherein a weave style of said sack-shaped fabric is a stretchable weave style.

* * * * *